(12) United States Patent
Yarnall et al.

(10) Patent No.: US 10,310,097 B2
(45) Date of Patent: Jun. 4, 2019

(54) GAMMA PROBE WITH HAND-PIECE CONTROL OF DETECTION PARAMETERS

(71) Applicant: Faxitron Bioptics, LLC, Marlborough, MA (US)

(72) Inventors: Stephen T. Yarnall, Poway, CA (US); Joel Kindem, Poway, CA (US); Richard L. Conwell, Poway, CA (US)

(73) Assignee: FAXITRON BIOPTICS, LLC, Marlborough, MA (US)

(*) Notice: Subject to any disclaimer, the term of this patent is extended or adjusted under 35 U.S.C. 154(b) by 519 days.

(21) Appl. No.: 14/902,796

(22) PCT Filed: Jul. 1, 2014

(86) PCT No.: PCT/US2014/045165
§ 371 (c)(1),
(2) Date: Jan. 4, 2016

(87) PCT Pub. No.: WO2015/003020
PCT Pub. Date: Jan. 8, 2015

(65) Prior Publication Data
US 2016/0170035 A1    Jun. 16, 2016

Related U.S. Application Data

(60) Provisional application No. 61/841,581, filed on Jul. 1, 2013.

(51) Int. Cl.
*A61B 6/00* (2006.01)
*G01T 1/161* (2006.01)
*A61B 6/12* (2006.01)

(52) U.S. Cl.
CPC .............. *G01T 1/161* (2013.01); *A61B 6/12* (2013.01); *A61B 6/4057* (2013.01);
(Continued)

(58) Field of Classification Search
CPC ....... A61B 6/12; A61B 6/4258; A61B 6/4057; A61B 6/4405; A61B 6/54; A61B 6/46
See application file for complete search history.

(56) References Cited

U.S. PATENT DOCUMENTS 5,036,201 A     7/1991  Carroll et al.
5,732,704 A  *  3/1998  Thurston .............. A61B 6/4258
                                                      250/336.1
(Continued)

FOREIGN PATENT DOCUMENTS

EP          2291679          3/2011

OTHER PUBLICATIONS

Korean Intellectual Property Office, International Search Report, International Application No. PCT/US2014/045165, dated Dec. 2, 2014, 6 pages.
(Continued)

*Primary Examiner* — Joel Lamprecht (57) ABSTRACT

Apparatus, techniques and systems are described for facilitating identification of a target area during a probe-guided radio-localization surgical procedure. The described apparatus, techniques and systems can be used to implement a nuclear-uptake mode controller integrated into a probe to allow a user to instantly switch between multiple nuclear-uptake modes directly from the probe hand-piece. For example, a nuclear-uptake mode controller integrated into the probe can be used to instantly switch between a high-sensitivity nuclear-uptake mode and a high-resolution nuclear-uptake mode to effectively identify the target area in the presence of interfering nuclear signals by better matching the probe's nuclear detection parameters to a search task for that target area.

21 Claims, 8 Drawing Sheets

(52) U.S. Cl.
CPC .......... *A61B 6/4258* (2013.01); *A61B 6/4405* (2013.01); *A61B 6/46* (2013.01); *A61B 6/54* (2013.01)

(56) References Cited

U.S. PATENT DOCUMENTS

| | | | |
|---|---|---|---|
| 5,857,463 | A | 1/1999 | Thurston et al. |
| 6,191,422 | B1 * | 2/2001 | Thurston ................. G01T 1/161 250/367 |
| 6,236,880 | B1 | 5/2001 | Raylman et al. |
| 6,263,232 | B1 | 7/2001 | Norman, Jr. |
| 6,331,703 | B1 | 12/2001 | Yarnall et al. |
| 6,771,802 | B1 * | 8/2004 | Patt ........................ G01T 1/161 378/140 |
| 6,940,071 | B2 | 9/2005 | Ramsden et al. |
| 7,202,478 | B2 | 4/2007 | Ramsden et al. |
| 8,816,292 | B2 | 8/2014 | Cui et al. |
| 9,069,092 | B2 * | 6/2015 | Oreper ................. G01T 1/2985 |
| 2003/0183768 | A1 | 10/2003 | Miller et al. |
| 2004/0054248 | A1 | 3/2004 | Kimchy et al. |
| 2005/0263711 | A1 | 12/2005 | Gerl et al. |
| 2014/0249402 | A1 * | 9/2014 | Kimchy ................. A61B 5/055 600/411 |

OTHER PUBLICATIONS

Extended European Search Report for European Patent Application No. 14819862.5, dated Dec. 5, 2016, 7 pages.

* cited by examiner

GAMMA PROBE WITH HAND-PIECE CONTROL OF DETECTION PARAMETERS

PRIORITY CLAIM AND RELATED PATENT APPLICATION

This application claims priority of U.S. Provisional Application No. 61/841,581 entitled "Gamma Probe with Hand-piece Control of Detection Parameters" and filed on Jul. 1, 2013. The entire disclosure of the above application is incorporated by reference as part of the disclosure of this application.

BACKGROUND

This application relates to devices, techniques and systems for detecting concentrations of injected radionuclides using a handheld nuclear update probe.

In medicine, handheld nuclear-uptake probes, with their audible feedback and count-rate readouts, are used to locate structures and regions where injected radionuclides are present, such as in radio-guided parathyroid and sentinel lymph node surgery with injected Tc-99 sestamibi and Tc-99 sulfur colloid radiotracers. Two important parameters for successful nuclear probe-guided surgery are the probe's high-energy photon sensitivity and its spatial resolution.

These parameters can be modified for a given probe in a number of ways. Increasing or decreasing the energy acceptance window can affect whether more or fewer scattered photons are counted. Widening the energy window increases photon sensitivity but decreases spatial resolution as more scattered high-energy photons are counted. Narrowing the energy window increases spatial resolution but decreases photon sensitivity as fewer scattered high-energy photons are counted.

SUMMARY

Devices, techniques and systems are described for facilitating identification of a target area during a probe-guided radio-localization surgical procedure. The described apparatus, techniques and systems can be used to implement a nuclear-uptake mode controller integrated into a probe to allow a user to instantly switch between multiple nuclear-uptake modes. For example, the nuclear-uptake mode controller integrated into the probe can be used to instantly switch between a high-sensitivity nuclear-uptake mode and a high-resolution nuclear-uptake mode to effectively identify the target area even in the presence of interfering nuclear signals by better matching the probe's nuclear detection parameters to a search task for that target area.

In one implementation, an apparatus for performing radio-localization of nuclear-emitting tissues is described to include a nuclear-uptake surgical probe with the ability to directly respond to operator inputs to change nuclear uptake parameters from inside the sterile surgical field. The apparatus can include one or more of the following features. The apparatus can potentially include a switch located on a hand-piece of the surgical probe for changing nuclear uptake parameters. The nuclear uptake parameters can include the photon energy acceptance window.

In another implementation, a method for performing a radio-guided surgical localization procedure is described to include modifying a photon energy acceptance window of a nuclear uptake gamma probe system from the sterile field during a surgical procedure.

In another implementation, described is a handheld nuclear-uptake surgical probe for performing radio-localization of nuclear-emitting tissues, nuclear-uptake surgical probe. The handheld nuclear-uptake surgical probe as described includes a nuclear-uptake mode controller configured to selectively switch between two or more nuclear-uptake modes of operation directly from the handheld nuclear-uptake surgical probe during the performance of radio-localization of nuclear-emitting tissues, wherein the two or more nuclear-uptake modes of operation have different nuclear-uptake parameters.

The handheld nuclear-uptake surgical probe as described can potentially include one or more of the following features. The nuclear-uptake mode controller can be configured to change the nuclear uptake parameters. The nuclear-uptake parameters can include photon energy acceptance window. The nuclear-uptake mode controller can be integrated into a handle of the handheld nuclear-uptake surgical probe. The nuclear-uptake mode controller can include a physical switch located on a handle of the handheld nuclear-uptake surgical probe to switch between the two or more nuclear-uptake modes of operation. The nuclear-uptake mode controller can include a touch screen located on a handle of the handheld nuclear-uptake surgical probe to switch between the two or more nuclear-uptake modes of operation. The nuclear-uptake mode controller can be sealed onto a handle of the handheld nuclear-uptake surgical probe to satisfy a sterile environment. The nuclear-uptake mode controller can be configured to receive an enclosure to seal the nuclear-uptake mode controller onto the handheld nuclear uptake surgical probe to satisfy a sterile environment. The handheld nuclear-uptake surgical probe can include a sensor unit for selectively detecting gamma photons associated with nuclear-emitting tissues in the two or more nuclear-uptake modes based on changes to the photon energy acceptance window. The handheld nuclear-uptake surgical probe can include a communication medium configured to exchange data with an external probe system control unit. The communication medium can include a wireless communication medium. The handheld nuclear-uptake surgical probe can include a report unit configured to provide feedback to a user, wherein the feedback includes information associated with the two or more nuclear-uptake modes of operation. The report unit can be integrated into the handheld nuclear-uptake surgical probe. Algorithms for generating the feedback can be different for each selectable nuclear-uptake mode. The feedback information associated with the two or more nuclear-uptake modes of operation can include identification of a currently selected one of the two or more nuclear-uptake modes of operation. The feedback information can include audible information.

In yet another implementation, a method of operating a handheld nuclear-uptake surgical probe is described. The method can include receiving, directly at a nuclear-uptake mode controller disposed on the handheld nuclear-uptake surgical probe, an input initiating a switch from one nuclear-uptake mode of operation to another nuclear-uptake mode of operation while the handheld nuclear-uptake surgical probe is in operation, wherein the two or more nuclear-uptake modes of operation have different nuclear-uptake parameters Responsive to the input received directly from the nuclear-uptake mode controller disposed on the handheld nuclear-uptake surgical probe, the handheld nuclear-uptake probe can switch to the other nuclear-uptake mode of operation.

The method can potentially include one or more of the following features. Responsive to the input received directly from the nuclear-uptake mode controller disposed on the handheld nuclear-uptake surgical probe, the handheld nuclear-uptake probe can modify a high-energy photon energy acceptance window of the handheld nuclear-uptake surgical probe associated with the other nuclear-uptake mode of operation. The method can include responsive to the input received directly from the nuclear-uptake mode controller disposed on the handheld nuclear-uptake surgical probe, outputting feedback information from a reporting unit of the handheld nuclear-uptake surgical probe, wherein the feedback information includes information associated with the nuclear-uptake modes of operation.

In yet another implementation, a method of operating a handheld nuclear-uptake surgical probe during a radio-localization surgical procedure is described. The method includes while the handheld nuclear-uptake surgical probe is in operation during the radio-localization surgical procedure, selectively switching between two or more nuclear-uptake modes of operation directly from the handheld nuclear-uptake surgical probe, wherein the two or more nuclear-uptake modes of operation have different nuclear-uptake parameters.

The method of operating a handheld nuclear-uptake surgical probe during a radio-localization surgical procedure can potentially include one or more of the following features. The method can include selectively switching between two or more nuclear-uptake modes of operation comprises modifying a high-energy photon energy acceptance window of the handheld nuclear-uptake surgical probe. The method can include selectively switching between two or more nuclear-uptake modes of operation directly from the handheld nuclear-uptake surgical probe is performed within a sterile surgical field.

In yet another implementations, described is a handheld nuclear-uptake surgical probe for performing radio-localization of nuclear-emitting tissues, the handheld nuclear-uptake surgical probe. The handheld nuclear-uptake surgical probe for performing radio-localization of nuclear-emitting tissues can include a collimator having an opening, the collimator configured to block gamma photons that are outside of collimator's field of view from passing through the collimator. The handheld nuclear-uptake surgical probe for performing radio-localization of nuclear-emitting tissues can include a gamma photon transparent window configured to block light from entering the opening of the collimator. The handheld nuclear-uptake surgical probe for performing radio-localization of nuclear-emitting tissues can include a scintillator configured to produce scintillation photons in proportion to energy of a gamma photon that passes through the collimator and enters the scintillator. The handheld nuclear-uptake surgical probe for performing radio-localization of nuclear-emitting tissues can include an optically-coupled photodiode configured to convert the scintillation photons produced by the scintillator to an induced charge pulse proportional to a number of the scintillation photons produced. The handheld nuclear-uptake surgical probe for performing radio-localization of nuclear-emitting tissues can include a backshield to block gamma photon signals from entering the optically-coupled photodiode from a back-end opposite of the collimator opening. The handheld nuclear-uptake surgical probe for performing radio-localization of nuclear-emitting tissues can include a signal processing unit configured to process the induced charge pulse into a voltage pulse with amplitude representing the energy of the incoming gamma photon for culling into a count of accepted voltage pulses. The handheld nuclear-uptake surgical probe for performing radio-localization of nuclear-emitting tissues can include a nuclear-uptake mode controller integrated into the handheld nuclear-uptake surgical probe, the nuclear-uptake mode controller configured to selectively switch between two or more nuclear-uptake modes of operation having different energy level acceptance windows used by the signal processing unit to obtain the count of accepted voltage pulses. The handheld nuclear-uptake surgical probe for performing radio-localization of nuclear-emitting tissues can include a wireless communication medium configured to exchange data with an external device.

The handheld nuclear-uptake surgical probe for performing radio-localization of nuclear-emitting tissues can potentially include one or more of the following features. The nuclear-uptake mode controller can be integrated into a handle of the handheld nuclear-uptake surgical probe. The nuclear-uptake mode controller can include a physical switch located on a handle of the handheld nuclear-uptake surgical probe to switch between the two or more nuclear-uptake modes of operation. The nuclear-uptake mode controller can be sealed onto a handle of the handheld nuclear-uptake surgical probe to satisfy a sterile environment. The nuclear-uptake mode controller can be configured to receive an enclosure to seal the nuclear-uptake mode controller onto the handheld nuclear uptake surgical probe to satisfy a sterile environment.

The above and other aspects, features and implementations are described in greater detail in the drawings, the description and the claims.

BRIEF DESCRIPTION OF THE DRAWINGS

Like reference symbols and designations in the various drawings indicate like elements.

DETAILED DESCRIPTION

Devices, techniques and systems described in this document can be used in various implementations to more quickly and accurately locate concentrations of radionuclides by allowing a user to quickly and more closely match a nuclear-uptake probe's response characteristics to a search task for locating concentrations of radionuclides. The gamma probe detection circuitry is designed to allow changing detection characteristics ('modes') using a probe-mounted switch. For example, when a user is surveying large areas of an anatomy, the user may prefer to start in a high-sensitivity mode that allows for faster probe movement and detection of faint or weak signals associated with the concentration of radionuclides emanating from deep structures or regions within the surveyed areas. Once the locations of the weak signals have been roughly identified, the user can switch to a high-resolution nuclear-uptake mode to slowly and more precisely locate the source of emissions such as is needed to guide a surgical dissection or to differentiate a focal signal emanating from a sentinel node near an interstitial radionuclide injection site.

There are a number of potential benefits to the above described nuclear-uptake mode switching approach. For example, smaller detectors, which can be contained in more compact probes tips, can be used to optimize or increase interstitial utility. Also, smaller detectors contain less of the high-energy photon sensing materials used to detect radionuclides, saving on costs. In addition, smaller detectors can be shielded and collimated using less high-Z material (e.g. Tungsten), with further cost savings. Implementations of the disclosed technology in this application can be used to provide a combination of a compact probe hand-piece with hand-piece-mounted controls for switching operational modes, enabling the surgeon to operate the probe in the sterile environment of the surgical field while quickly and easily switching back and forth between multiple nuclear-uptake modes, in-situ, without leaving the sterile surgical field. This combination can expedite and improve the search task for identifying the locations of the concentration of radionuclides within the survey areas without assistance from others outside the sterile field including the operating room staff.

The described devices, techniques and systems can potentially improve nuclear probe-guided localization of radiation-emitting tissues. Of particular interest, is increasing the utility of a handheld probe during surgery by providing user-control of energy window acceptance parameters, the benefits of which include expediting the localization, the ability to reduce the probe's size and invasiveness, and to minimize the probe's cost. Moreover, the user (e.g., a surgeon) can operate the probe to isolate the location of the radiation-emitting tissues from start to finish without any interruption or without needing to look away or move away from the target radiation-emitting tissues.

The energy window of a given nuclear-uptake probe has been normally set to provide the best or ideal compromise between high-energy photon sensitivity and rejection of Compton-scatter. In this way, the user can achieve a balance between the nuclear-uptake probe's performance in quickly surveying for radioactive hotspots or radiation-emitting tissues and in precisely localizing a radioactive region or structure. A wider energy window allows more accepted voltage pulses, known as "counts," converted from detected photons that can be used by the nuclear-uptake probe's count-rate processor to produce user feedback with less statistical variation, while allowing a shorter count-rate calculation response—together providing improved count-rate feedback fidelity. This allows the user to move the nuclear-uptake probe faster and to survey wide areas (e.g. multiple nodal basins) in less time or to look for faint signals (e.g. deep-set sentinel nodes). Narrower energy windows reject more Compton-scatter, improving the probe's spatial resolution and allowing the user to more precisely locate focal regions or structures and to locate radioactive hot spots near the radionuclide injection site.

The described devices, techniques and systems allow the user to quickly change the nuclear-uptake parameters of a nuclear-uptake probe from the sterile surgical field without changing the probe. Various technical features of the device, techniques and systems, and associated examples are described in this document.

Handheld Multi-Mode Nuclear-Uptake Probe

Figure 1:
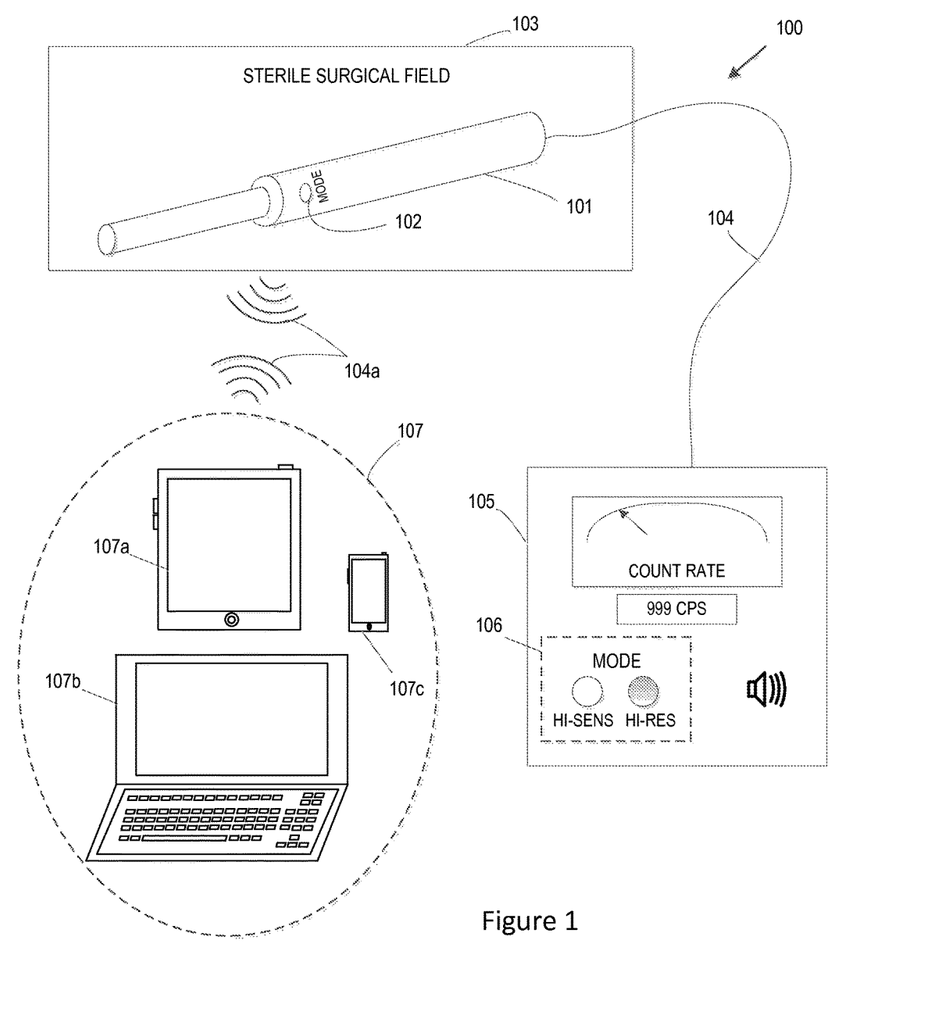
FIG. 1 shows a perspective view of an exemplary nuclear-uptake probe system.

FIG. 1 shows a perspective view of an exemplary nuclear-uptake probe system 100, including a processing device, such as an external probe system control unit 105, for processing the counts data received from a nuclear-uptake probe hand-piece 101 (i.e., a handheld probe). A nuclear-uptake mode controller, such as mode switch 102, is located on and integrated into the nuclear-uptake probe hand-piece 101, giving the user direct access to a mechanism for changing or switching between multiple energy acceptance windows from a sterile surgical field 103. The user can switch between multiple nuclear-uptake modes by simply interacting with the mode switch 102 without interruption and without having to move or look away from the tissue area being surveyed. Thus, the user is able to identify the location of the concentration of radionuclide emitting signals from deep structures or regions within the surveyed area. A communication medium, such as cable 104, can be used to transmit electronic signals between the handheld probe and the external probe system control unit 105. In some implementations, cable 104 could be replaced by a wireless connection such as an RF wireless link to provide more freedom in moving the nuclear-uptake probe hand-piece 101, around during surgery. The external probe system control unit 105, may include an indicator 106, displaying the current energy acceptance window mode selection. The indicator 106, can display the selected energy acceptance window using various graphical presentations including physical indicator lights integrated into the external probe system control unit 105, virtual indicator lights displayed on a display device (not shown), names of the selected nuclear-uptake modes displayed on a display device, or other similar visual indications.

In some implementations, the indicator 106 can include an audio indicator in addition to, or instead of, a visual indicator. Examples of audio indicators include various audible sounds that identify the selected nuclear-uptake mode to the surgeon without requiring the surgeon to look at a display panel or indicator on the external probe system control unit 105. The various audible sounds can include different tones to represent different modes or the actual names of the different modes. In addition, other similar visual and audio indicators can be implemented.

In some implementations, the visual and/or audio indicators can be integrated into the nuclear-uptake probe hand-piece 101 in order to provide feedback that identifies the selected nuclear-uptake mode without distracting or interrupting the user. Thus, the user can obtain feedback on the selected nuclear-uptake mode without interruption and without moving away or looking away from the survey area.

Figure 2A:
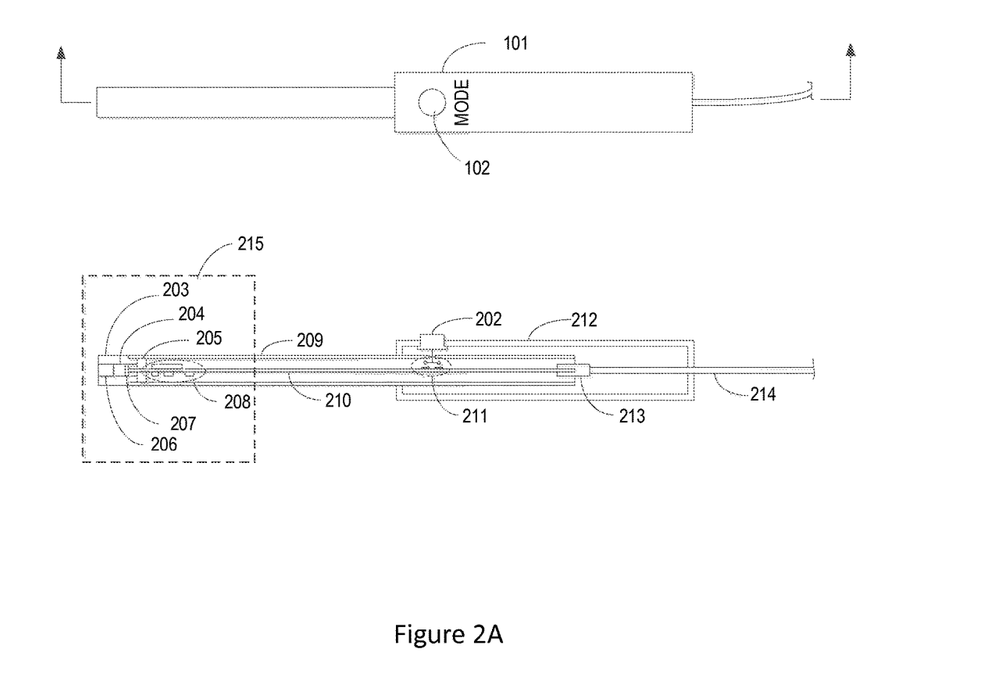
FIG. 2A shows a cross sectional side view of an exemplary nuclear-uptake probe hand-piece.
Figure 2B:
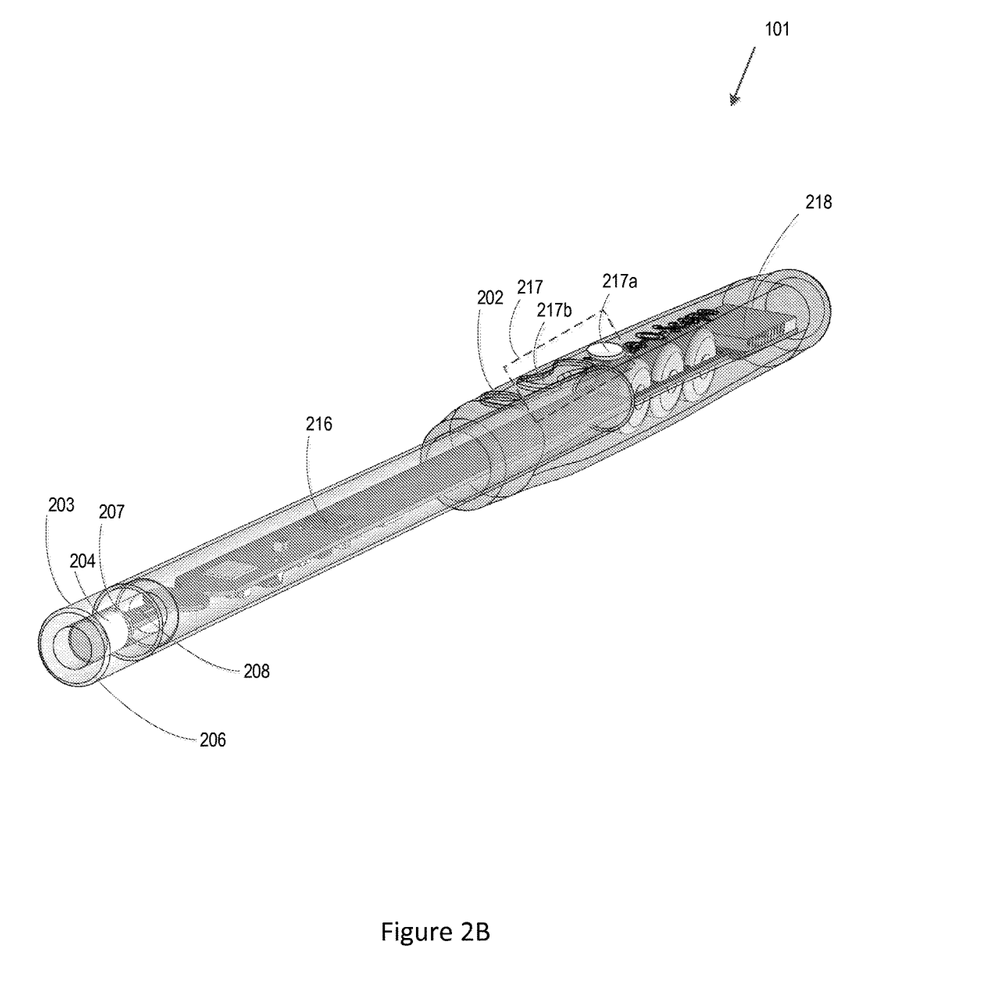
FIG. 2B shows a three-dimensional perspective view of an exemplary nuclear-uptake probe hand-piece.

FIG. 2A shows a cross sectional side view of an exemplary nuclear-uptake probe hand-piece 101 and FIG. 2B shows a three-dimensional perspective view of an exemplary nuclear-uptake probe hand-piece. FIGS. 2A and 2B in combination illustrate various components integrated into the exemplary nuclear-uptake probe hand-piece. As shown, the nuclear-uptake probe hand-piece 101 has an integrated mode switch 102, such as push-button switch 202, at least partially protruding through handle 212, for switching between multiple nuclear-uptake modes. Each of the multiple nuclear-uptake modes has different nuclear-uptake parameters, such as the energy acceptance window of the handheld nuclear-uptake probe during operation. Different energy acceptance windows of the handheld nuclear-uptake probe are described with respect to FIG. 3 below. Thus, switching between different nuclear-uptake modes of operation changes the energy acceptance window of the handheld nuclear probe during operation.

Handle 212 is designed to allow one-handed operation of the nuclear-uptake probe hand-piece 101. For example, the one-handed operation includes having the integrated mode switch 102, such as push-button switch 202, positioned on the handle 212, for actuation by at least a finger of a user while holding the nuclear-uptake probe hand-piece in one-hand, the same hand whose at least one finger is used to actuate the integrated mode switch 102.

The nuclear-uptake probe hand-piece 101 includes a gamma photon sensor unit 215, to sense or detect gamma photons. The gamma photon sensor unit 215 includes integrated collimator 203 for collimating or directing gamma photons, scintillator 204 for converting the received gamma photons into optical photons and optically-coupled photodiode 207 for collecting and detecting the optical photons from the scintillator 204. Integrated collimator 203 works in conjunction with multi-mode operation of the nuclear-uptake probe hand-piece to block gamma photons that are outside of its field of view from entering scintillator 204. The physical opening of collimator 203 is sealed by a gamma-ray transparent window 206, which blocks ambient light from reaching the photodiode 207. This gamma-ray transparent window 206 may be made of a range of suitable materials including, e.g., a biocompatible and hermetic sealant such as silicone. When a gamma-ray passes through the opening in collimator 203, the gamma-ray enters scintillator 204, producing scintillation photons in proportion to the gamma ray energy. The techniques described in this document can be used to obtain uniform light collection from scintillator 204, such as a Cesium Iodide (CsI) scintillating crystal or similar materials. Obtaining uniform light collection from scintillator 204 can be an enabling factor in obtaining a fine energy resolution, e.g., 10% energy resolution. Scintillation photons are converted by the optically-coupled photodiode 207 into an induced charge pulse proportional to the number of scintillation photons. The optically-coupled photodiode 207 can include low leakage current photodiodes, which further enables fine energy resolution.

The nuclear-uptake probe hand-piece 101 also includes a signal processing unit such as front-end electronics 208 to process the induced charge pulse into a voltage pulse with amplitude representing the energy of the incoming gamma photon for potential culling by energy acceptance window processor 216 into a 'count', which is processed to provide user feedback. The energy window acceptance processor can be implemented using a low cost microprocessor or other similar processing devices and may perform other functions in the handheld nuclear-uptake probe. Front-end electronics 208 can include processing circuitry, such as a low power, mixed signal application specific integrated circuit (ASIC) to perform enhanced or near optimal charge integration and signal conditioning for scintillator 204 and optically-coupled photodiode 207. An ASIC can be a system-on-chip (SoC) that includes microprocessors, memory blocks including ROM, RAM, EEPROM, flash memory and other large building blocks. In some implementations, front-end electronics 208 can include field-programmable gate arrays (FPGA). Programmable logic blocks and programmable interconnects allow the same FPGA to be used in many different applications. The front-end electronics as described can enable automatic compensation for variations in manufacturing and environmental conditions, to achieve at least a 90-electron noise budget at room temperature, for example.

The energy acceptance window processor 216 may be located in the probe hand-piece 101 or the external probe system control unit 105. Printed circuit assembly 210 contains mode switch contacts 211 that sense user input in response to the user interfacing with the nuclear-uptake mode switch 102 to change or switch between multiple nuclear-uptake modes and thus switch between multiple energy-window acceptance modes (i.e., nuclear-uptake modes) by depressing switch actuator 202. The necessary electronics for the nuclear-uptake mode switch 102 are contained in cannula 209, which can also provide EMI shielding for the sensitive front-end low-noise sensing components.

Nuclear-uptake probe hand-piece 101 can also include additional control units such as control and report unit 217 that allows the user to access and control various probe functions on the nuclear-uptake probe hand-piece 101. The additional control units such as control and report unit assembly 217 can be implemented using multiple user interface elements (e.g., buttons, toggle switches, dials, etc.), and the number of user interface elements employed can be at least partially dependent on the number of control functions implemented into a design. In the example shown in FIG. 2B, the additional control units such as control and report unit assembly 217 is shown with three additional user interface elements. Count rate controller 217a can be implemented as a button associated with obtaining the count rate during the search mode. Pressing and holding the count rate controller button 217a can initiate the extended count rate function to determine whether a statistically significant count rate can be obtained, and if it can be obtained, its count rate value. To alert the user of the extended count rate operating during a scan mode, an audible alert message can be broadcasted to request that the user hold steady the handheld nuclear-uptake probe hand-piece 101. An example of the broadcast message may be: "Extended count, please hold the probe steady." Once a hotspot of the concentration of injected radionuclides has been identified, the handheld nuclear-uptake probe hand-piece 101 can be switched between multiple modes (e.g., search and scan modes) while identifying other tissue areas that may be within some predetermined range (e.g., 10%) in comparison to the signal detected from the hotspot to identify which tissues should be excised.

In the example shown in FIG. 2B, control and report unit 217 can also include a range controller 217b implemented as a toggle switch. The range controller 217b can be used to control the volume of any audible feedback based on the signal from the handheld nuclear-uptake probe hand-piece 101, for example from external probe system control unit 205. The range controller 217b can also be used to vary the audio feedback signal range in comparison to the input count range. In some implementations, the nuclear-uptake mode controller 102 and associated button 202 can be integrated with the other user interface elements such as control and report unit 217.

Control and report unit 217 also provides voice or audio reporting/feedback during surgery to enable the user (e.g., a surgeon) to maintain her visual focus on the target incision site. The reporting/feedback includes information associated with the multiple nuclear-uptake modes. For example, the reporting/feedback information can include information to identify the currently selected nuclear-uptake mode. Also, the reporting/feedback information can include listing of choices of the multiple nuclear-uptake modes available for the user to select. In addition, the reporting/feedback information can be processed using algorithms that are different for each mode selected. For example, audio feedback may be filtered differently in high-sensitivity mode than it is in high-resolution mode to improve its stability or response time. Reporting/feedback during the operation of the nuclear-uptake probe hand-piece 101 can be implemented using techniques other than voice or audio. For example, various tactile feedback techniques such as haptic feedback can be used. Other alternatives include visual feedback such as by varying the intensity, brightness, color and/or on/off frequency of one or more lights as the nuclear-uptake probe hand-piece is moved closer or away from the location of the concentration of injected radionuclides.

As described with respect to FIGS. 1, 2A and 2B above, the wired communication medium 104 can be implemented by providing a connector 213 for physically connecting data communication wire 214 to printed circuit assembly 210. Alternatively, the handheld nuclear-uptake probe hand-piece 101 can communicate with an external device using one or more wireless communication links 104a. For example, Bluetooth Low Energy (BLE) circuitry 218 can be used to enable low cost, battery driven wireless link to external probe system control unit 105 or other computing devices 107 for exchanging data and/or commands with the nuclear-uptake probe hand-piece. Other examples of wireless connectivity include 802.11 family of WiFi technologies. Examples of the computing devices 107 capable of wirelessly communicating with the nuclear-uptake probe hand-piece include portable computing devices, such as a tablet computer 107a, a laptop 107b, a smart phone 107c, iPad, and wearable devices include a smart watch.

Mode switch 102, such as push button switch 202 and associated mode switch contacts 211 are integrated into the nuclear-uptake probe hand-piece 101 in a manner appropriate for the sterile environment of a surgical field. Various techniques can be implemented to maintain a sterile environment. For example, mode switch 102, such as push button switch 202 and associated mode switch contacts 211 can be sealed into the nuclear-uptake probe hand-piece 101 to satisfy sterile environment. In some implementations, a hermetic seal can be used. Alternatively, mode switch 102, such as push button switch 202 and associated mode switch contacts 211 can be designed or packaged to receive or interface with a separate device that prevents biological materials, chemicals, fluids and other surgical materials from entering the nuclear-uptake probe hand-piece during surgery. For example, mode switch 102, such as push button switch 202 and associated mode switch contacts 211 can be designed or packaged to receive or interface with a cap, cover, housing, a surgical drape, and other like materials and devices that provides a seal to satisfy sterile environment. In addition, the nuclear-uptake probe hand-piece 101 can be manufactured as a sterile disposable device.

Figure 2C:
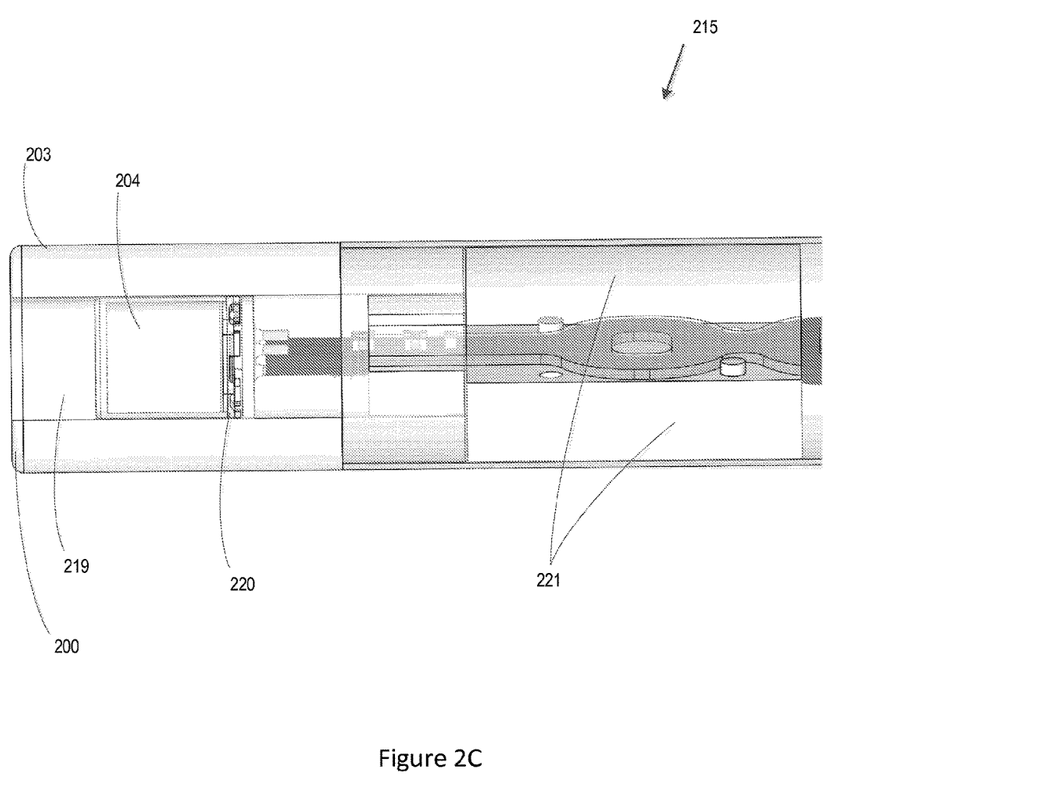
FIG. 2C shows a cross sectional side view of an exemplary sensor unit of a nuclear-uptake probe hand-piece.
Figure 2D:
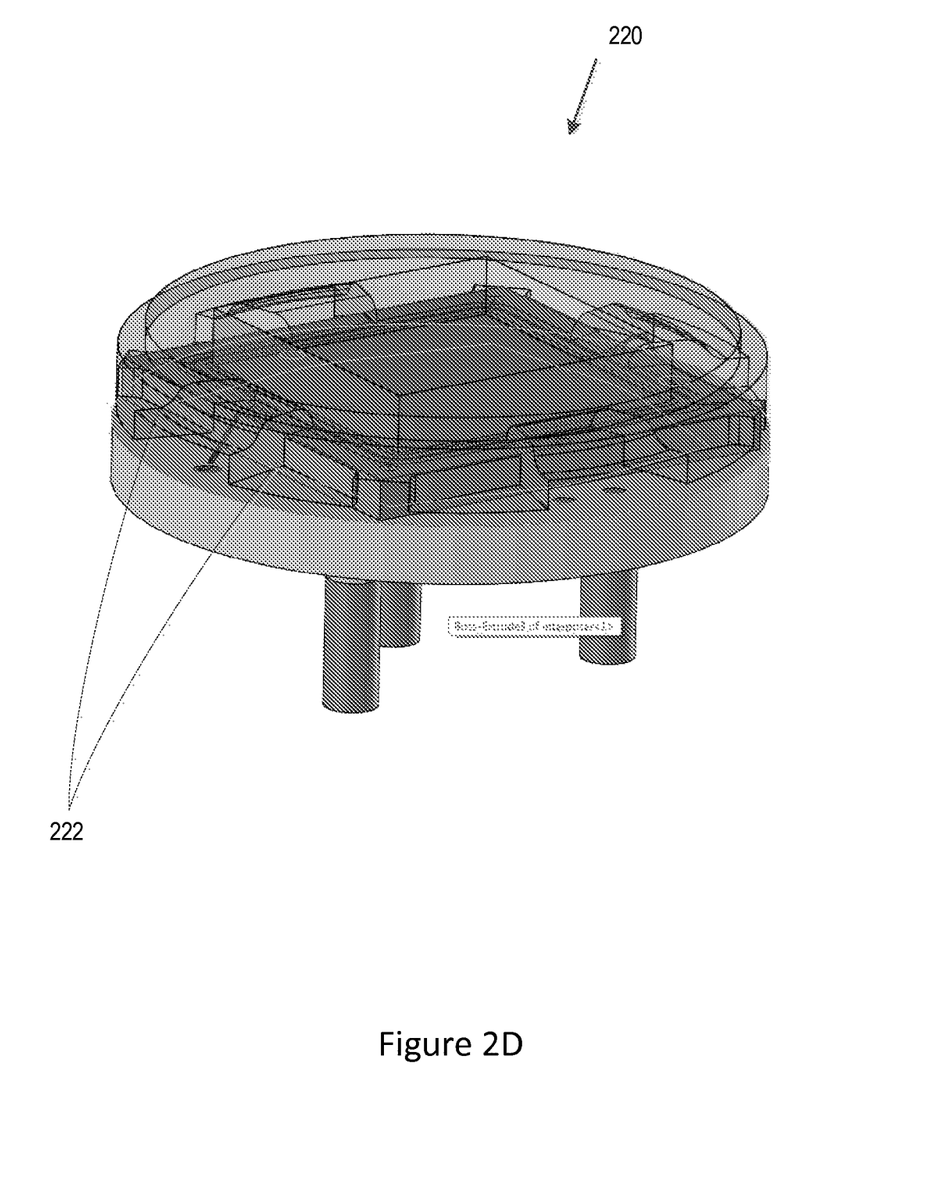
FIG. 2D shows a three-dimensional perspective view of an exemplary optical light guide and reflector unit of a nuclear-uptake probe hand-piece.

FIG. 2C shows a cross sectional side view of an exemplary sensor unit of a nuclear-uptake probe hand-piece. FIG. 2D shows a three-dimensional perspective view of an exemplary optical light guide and reflector unit of a nuclear-uptake probe hand-piece. FIGS. 2C and 2D in combination show optically related components that provide for a highly efficient sensor unit 215 to detect gamma photons emitted from the concentration of injected radionuclides. Sensor unit 215 can include optical components that enable a highly efficient photon detection/sensor. Integrated collimator 203, selectively blocks gamma photons that are outside of its field of view from entering scintillator 204. It includes low-Z and low density optical blocking plug 219 at the front end to prevent ambient light from entering scintillator 204. Optical reflector and light guide 220 are placed next to the scintillator 204, allowing for uniform light collection from the scintillator 204 (e.g., a CsI scintillating crystal).

Optical light guide and reflector 220 is shown in further detail in FIG. 2D. In an exemplary design, optical light guide and reflector 220 can route around wire bonds for ease of manufacture. Optical light guide and reflector 220 provides substantially optimal light collection even for the thicker bond line required by the need for wire bonding due to front side illumination because optical light guide and reflector 220 is an optical diffuse reflector with high reflectivity. Without this design, light collection would be suboptimal. Optical light guide and reflector 220 can be pre-molded out of optically reflective material, which makes the assembly process easy and fast (versus potting with reflective epoxy), and also has better optical performance Self fixturing, which keys off of the outline of the photodiode, eases assembly. Also, additional cutouts can be used to simplify assembly. In the example shown in FIG. 2D, there are 4 cutouts even though there are only two wire bonds so the operator does not need to have it aligned to the correct polarity. Optical light guide and reflector 220 can be designed to have a snap-lock (similar to a Lego® block, for example) interface to the upper reflector, holding the crystal which makes it easy to handle and attach with an optical medium (epoxy/silicone/grease, etc.).

The sensor unit 215 includes backshield 221 disposed after the front-end electronics to block or shield the sensing unit 221 against gamma photon signals entering from a backend (e.g., opposite end of the probe tip) towards the tip of the nuclear-uptake probe hand-piece 101. In an exemplary design, the backshield 221 includes two half cylinders of backshield material, a sandwich board and a plug that goes through the center so to provide back gamma shielding. Also, backshield 221 acts as electrical grounding. Backshield 221 can be formed using an injection molded tungsten part to achieve low cost. In addition to providing back gamma photon shielding, backshield 221 provides electromagnetic interference (EMI) shielding for radio frequency (RF) signals from the wireless circuitry 218. For ease of manufacture, the backshield 221 can be formed to have interlocking tabs and a symmetric design.

The design of the described sensor unit 215, including the individual components provides for substantially optimal light collection and thus efficient and optimal gamma photon detection with fine resolution. Because of the efficiency and fine resolution of the sensor unit 215, the ability to switch between different nuclear-uptake (or energy acceptance window) modes from the nuclear-uptake probe hand-piece 101, without leaving the sterile surgical field becomes advantageous. Furthermore, the detector material type and design provide for improved peak to total counts (e.g. there is no hole tailing such as is the case with CZT/CdT based detectors) which would prohibit the practical implementation of such mode switching due to the reduction in efficiency resulting from a narrow energy window.

While FIGS. 2A, 2B, 2C and 2D show an example implementation of a single push button 102, with associated switch actuator 202, and mode switch contacts 211, more than one push button 102, can be used. For example, a separate dedicated push button can be used to represent each nuclear-uptake mode. In the multi-push button example, multiple switch actuators 202, and switch contacts 211, may be needed.

The nuclear-uptake mode switch 102, and the associated switch contacts 211, are not limited to a push-button. Other physical and virtual switch mechanisms that perform substantially the same functions can be implemented. Examples of physical switch mechanism include rotary dials, multidirectional toggle switches, slide switches, and other similar physical switches. Examples of virtual switch mechanisms include touch sensitive areas on a touchscreen or touchpad that sense physical touch or capacitive charge differences in response to a user touching or hovering near the touch sensitive areas corresponding to different nuclear-uptake modes. In some implementations, touch-free input mechanisms can replace the physical and virtual switches. Examples of touch-free input mechanisms include voice activation and gesture or motion detection and tracking.

Nuclear Photon Detection and Signal Processing Using Multi-Mode Switching

Figure 3:
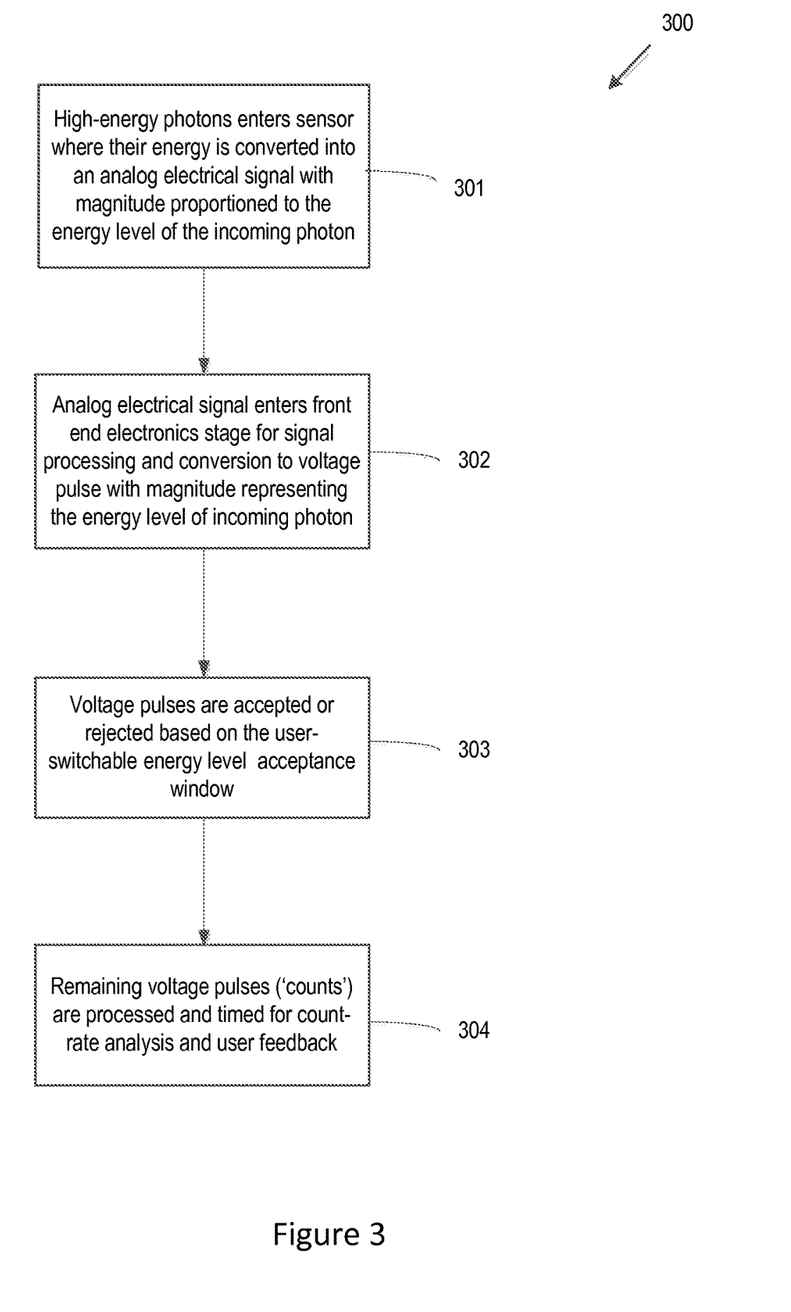
FIG. 3 shows a block diagram illustrating an exemplary process of sensing a nuclear photon, then processing the photon for user feedback.

FIG. 3 shows a block diagram illustrating an exemplary process 300 of sensing/detecting a nuclear photon, then processing the sensed/detected photon for user feedback. Sensing/detection process 301 occurs in a sensor, such as the gamma photon sensor unit 215, to capture all detectable events regardless of their energy. Signal processing/front-end electronics process 302, is performed in front-end circuitry/electronics, such as front-end electronics 208, to convert analog output signal from sensing process 301, into a voltage pulse, with the magnitude proportional to the energy of the incoming gamma photon. In energy spectrum analyzer process 303, the voltage pulses from the signal processing/front-end electronics process 302, are accepted or rejected based on the application of the selected energy acceptance window. This process can be changed/switched by depressing the push-button switch actuator 202. In user feedback process 304, accepted voltage pulses (i.e., counts) are processed and timed for count-rate analysis and user feedback.

Figure 4:
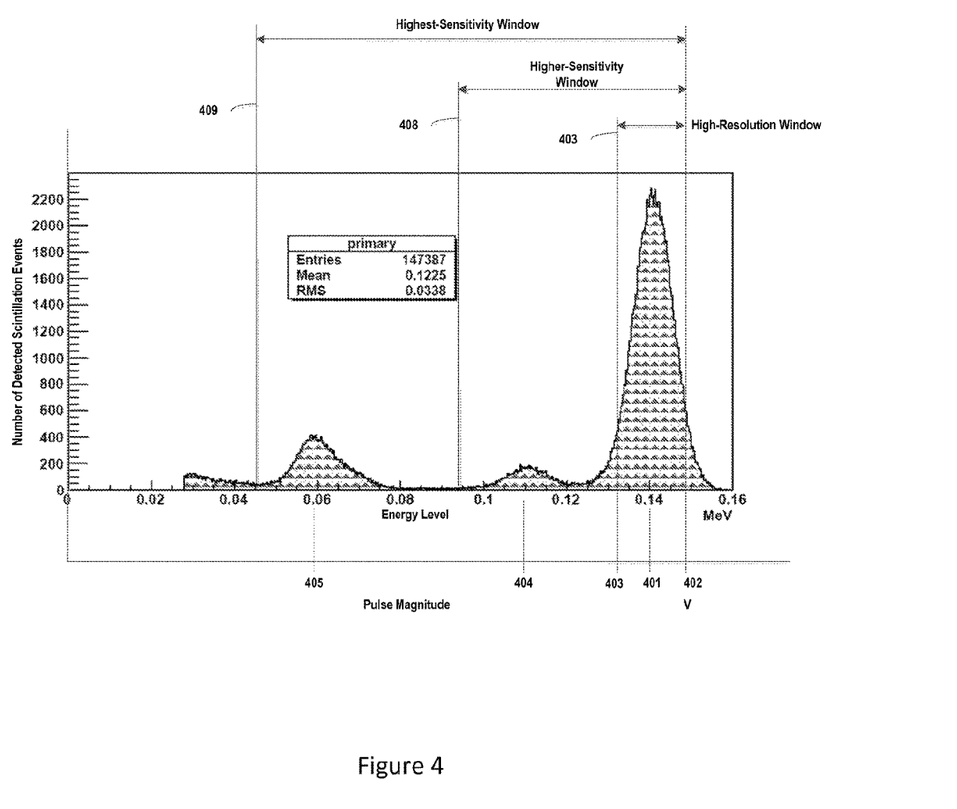
FIG. 4 shows an energy spectrum of an exemplary nuclear-uptake probe.

FIG. 4 shows an energy spectrum of an exemplary nuclear-uptake probe. Specifically, shown in FIG. 4 is a typical spectrum plot of energy levels of gamma photons accumulated by the nuclear-uptake probe 101, over a fixed time period with corresponding probe output voltage levels for the radioisotope Tc-99. The 141 KeV full-energy gamma ray peak 401, the Cesium Iodide (CsI) escape peak 404, and the X-ray fluorescence peak 405 (Kalpha and Kbeta emission from the inside of the collimator 203 stimulated by incident gamma-rays), are shown. Detected events with an energy level below the X-ray energy peak 405 are caused by electronic noise and low level background. They are removed by a hardware-based low level discriminator which selects only events with energy above this threshold. Cutoff lines 403, 408, and 409 demonstrate three potential and different lower energy cutoffs, and cutoff line 402 represent the higher energy cutoff or upper level discriminator. The first, at cutoff line 409, depicts a threshold that would produce a relatively high count-rate but that would include more scattered gamma photons including off-angle photons that enter the collimator 203, but fail to reach the scintillator 204; the second, at cutoff line 408, that would provide higher scatter rejection of off-angle photons but with a lower count rate; and the third, at cutoff line 403 that would provide even higher scatter rejection than at cutoff line 408, but with an even lower count-rate. Depressing nuclear-uptake mode switch 102 can switch between cutoff lines 403, 408 and 409 to produce higher-resolution or higher count rates. In the example shown in FIG. 4, the highest-sensitivity window is illustrated to cover the energy level range from cutoff line 409 to cutoff line 402. The higher-sensitivity window is illustrated to cover the energy level range from cutoff line 408 to cutoff line 402. The high-resolution window is illustrated to cover the energy level range from cutoff line 403 to cutoff line 402.

Example Nuclear Localization Procedure Using Multi-Mode Handheld Probe

Figure 5:
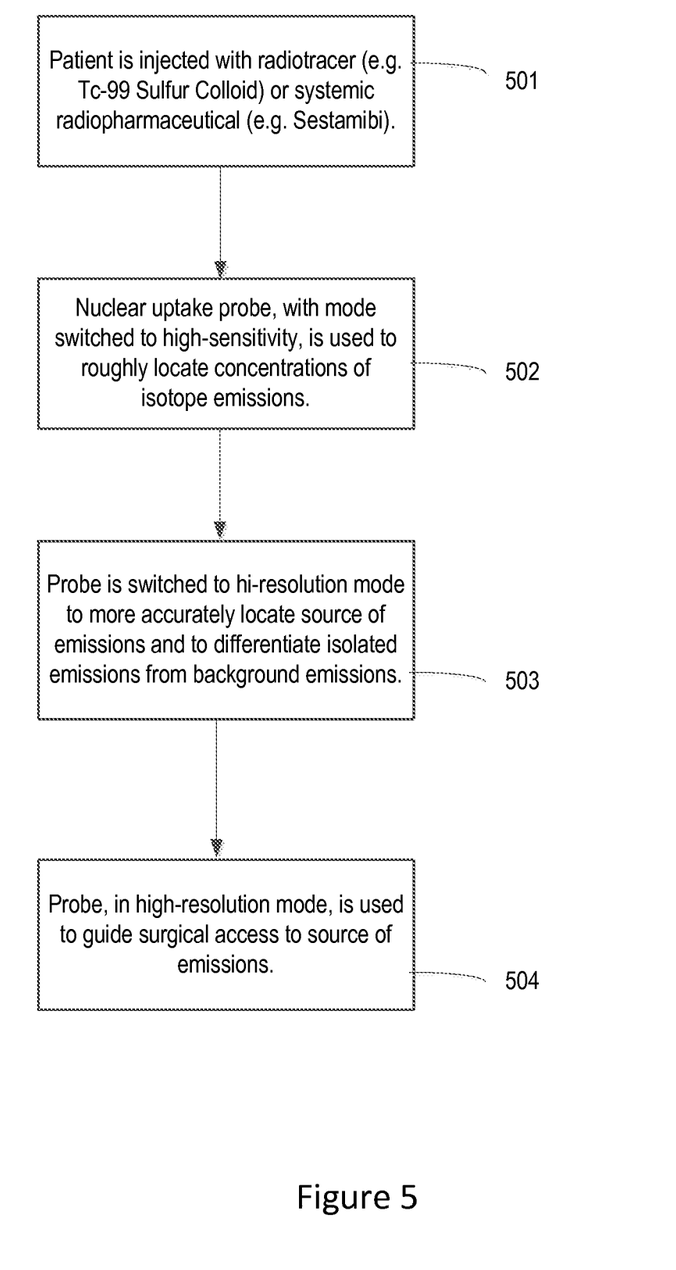
FIG. 5 shows a flow diagram of an exemplary nuclear localization procedure using a multi-mode handheld probe.

FIG. 5 shows a flow diagram of an exemplary nuclear localization procedure performed using a multi-mode handheld probe. First, in step 501, the patient is injected interstitially with a dose of tracer (e.g. Tc-99 Sulfur Colloid as for locating sentinel nodes), or systemically with a dose of radioisotope-containing pharmaceutical (e.g. Tc-99 Sestamibi as for locating parathyroid adenomas). An appropriate time is allocated for allowing the dose to concentrate according to its biological interaction. In step 502, the multi-mode nuclear-uptake handheld probe as described in this document is deployed in high-sensitivity mode to survey for the location of concentrated radioisotope emissions. The use of high-sensitivity mode allows the user to move the probe more quickly thanks to the relative abundance of high-energy photon counts that are available for audio-feedback. When a location of concentrated radioisotope emissions is identified, the multi-mode nuclear-uptake handheld probe can be switched as in step 503, to operate in high-resolution mode to more precisely locate the source of emissions and to better differentiate focal sources from background emissions. Once the location of the source has been precisely identified, the multi-mode nuclear-uptake handheld probe still in high-resolution mode can be used as in step 504, to guide the dissection of the anatomical structure or region. The small probe tip enabled by the devices, techniques and systems described in this document can potentially minimize surgical access requirements while improving visualization of the dissection. Moreover, the small probe tip provides fine spatial resolution for discriminating between closely-spaced anatomical structures.

Accordingly, it is to be understood that the embodiments and implementations of the devices, techniques and systems described herein are merely illustrative of various potential applications. Potential variations to the devices, techniques and systems described in this document can include, for example, 1) the use of other methods that could be made available to the user to change the uptake parameters from the sterile surgical field such as voice commands, gestures, or foot-pedals; 2) methods other than changing the energy acceptance that would result in a change to the sensitivity and/or the resolution such as electrically switching between different on-board sensor configurations; and 3) the use of other high-energy photon sensors such as bulk semiconductors (e.g. CZT or CT) or crystal scintillators coupled to photomultiplier tubes.

While this document contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this document.

What is claimed is:

1. A handheld nuclear-uptake surgical probe for performing radio-localization of nuclear-emitting tissues, nuclear-uptake surgical probe comprising:
a handle;
a nuclear-uptake mode controller configured to selectively set a photon energy acceptance window of the handheld surgical probe; and
a switch located on the handle and communicatively coupled to the nuclear-uptake mode controller to selectively initiate setting of the photon energy acceptance window.

2. The handheld nuclear-uptake surgical probe of claim 1, wherein the nuclear-uptake mode controller is integrated into a handle of the handheld nuclear-uptake surgical probe.

3. The handheld nuclear-uptake surgical probe of claim 1, wherein the switch comprises a physical switch.

4. The handheld nuclear-uptake surgical probe of claim 1, wherein the switch comprises a touch screen.

5. The handheld nuclear-uptake surgical probe of claim 1, wherein the nuclear-uptake mode controller is sealed onto the handle of the handheld nuclear-uptake surgical probe to satisfy a sterile environment.

6. The handheld nuclear-uptake surgical probe of claim 1, wherein the nuclear-uptake mode controller is configured to receive an enclosure to seal the nuclear-uptake mode controller onto the handle to satisfy a sterile environment.

7. The handheld nuclear-uptake surgical probe of claim 1, comprising a sensor unit for selectively detecting gamma photons associated with nuclear-emitting tissues based at least in part on changes to the photon energy acceptance window.

8. The handheld nuclear-uptake surgical probe of claim 1, comprising a communication medium configured to exchange data with an external probe system control unit.

9. The handheld nuclear-uptake surgical probe of claim 1, wherein the communication medium comprises a wireless communication medium.

10. The handheld nuclear-uptake surgical probe of claim 1, comprising a report unit configured to provide feedback to a user, wherein the feedback includes information associated with the selectively set photon energy acceptance window.

11. The handheld nuclear-uptake surgical probe of claim 1, wherein the report unit is integrated into the handle of the handheld nuclear-uptake surgical probe.

12. The handheld nuclear-uptake surgical probe of claim 10, wherein algorithms for generating the feedback are based at least in part on the selectively set photon energy acceptance window.

13. The handheld nuclear-uptake surgical probe of claim 10, wherein the feedback information associated with the selectively set photon energy acceptance window includes identification of a currently set photon energy acceptance window.

14. The handheld nuclear-uptake surgical probe of claim 10, wherein the feedback information comprises audible information.

15. A method of operating a handheld nuclear-uptake surgical probe, the method comprising:
receiving an input from a switch on the handheld nuclear-uptake surgical probe while the handheld nuclear-uptake surgical probe is in operation; and
responsive to the input, switching a photon energy acceptance window of the nuclear-uptake surgical probe.

16. The method of claim 15, comprising:
responsive to the input, outputting feedback information from a reporting unit of the handheld nuclear-uptake surgical probe, wherein the feedback information includes information associated with the photon energy acceptance window of the nuclear-uptake surgical probe.

17. A handheld nuclear-uptake surgical probe for performing radio-localization of nuclear-emitting tissues, the handheld nuclear-uptake surgical probe comprising:
a collimator having an opening, the collimator configured to block gamma photons that are outside of collimator's field of view from passing through the collimator;
a gamma photon transparent window configured to block light from entering the opening of the collimator;
a scintillator configured to produce scintillation photons in proportion to energy of a gamma photon that passes through the collimator and enters the scintillator;
an optically-coupled photodiode configured to convert the scintillation photons produced by the scintillator to an induced charge pulse proportional to a number of the scintillation photons produced;
a backshield to block gamma photon signals from entering the optically-coupled photodiode from a backend opposite of the collimator opening;
a signal processing unit configured to process the induced charge pulse into a voltage pulse with amplitude representing the energy of the incoming gamma photon for culling into a count of accepted voltage pulses;
a switch disposed on the handheld nuclear-uptake surgical probe;
a nuclear-uptake mode controller integrated into the handheld nuclear-uptake surgical probe, the nuclear-uptake mode controller operatively coupled to the switch and configured to selectively switch a photon energy acceptance window of the handheld nuclear-uptake surgical probe; and
a wireless communication medium configured to exchange data with an external device.

18. The handheld nuclear-uptake surgical probe of claim 17, wherein the nuclear-uptake mode controller is integrated into a handle of the handheld nuclear-uptake surgical probe.

19. The handheld nuclear-uptake surgical probe of claim 17, wherein the physical switch located on a handle of the handheld nuclear-uptake surgical probe.

20. The handheld nuclear-uptake surgical probe of claim 17, wherein the nuclear-uptake mode controller is sealed onto a handle of the handheld nuclear-uptake surgical probe to satisfy a sterile environment.

21. The handheld nuclear-uptake surgical probe of claim 17, wherein the nuclear-uptake mode controller is configured to receive an enclosure to seal the nuclear-uptake mode controller onto the handheld nuclear uptake surgical probe to satisfy a sterile environment.

* * * * *